(12) United States Patent
Kirshner et al.

(10) Patent No.: US 10,295,476 B1
(45) Date of Patent: May 21, 2019

(54) SYSTEM AND METHOD FOR MULTIPLE MODE INSPECTION OF A SAMPLE

(71) Applicant: Applied Materials Israel Ltd., Rehovot (IL)

(72) Inventors: Binyamin Kirshner, Elkana (IL); Yehiel Kapoano, Omer (IL)

(73) Assignee: Applied Materials Israel Ltd., Rehovot (IL)

( * ) Notice: Subject to any disclaimer, the term of this patent is extended or adjusted under 35 U.S.C. 154(b) by 0 days.

(21) Appl. No.: 16/103,535

(22) Filed: Aug. 14, 2018

(51) Int. Cl.
| | |
|---|---|
| G01N 21/88 | (2006.01) |
| G01N 21/95 | (2006.01) |
| G02B 26/08 | (2006.01) |
| G02B 27/10 | (2006.01) |

(52) U.S. Cl.
CPC ..... *G01N 21/8806* (2013.01); *G01N 21/9501* (2013.01); *G02B 26/0816* (2013.01); *G02B 27/10* (2013.01); *G01N 2021/8825* (2013.01); *G01N 2021/8848* (2013.01)

(58) Field of Classification Search
CPC ............... G01N 21/88; G01N 21/8803; G01N 21/8806; G01N 21/95; G01N 21/9501; G01N 2021/8822; G01N 2021/8825; G01N 2021/8834; G01N 2021/8845; G01N 2021/8848; G02B 26/08; G02B 26/0816; G02B 26/0875; G02B 23/02; G02B 23/06; G02B 23/08; G02B 27/10
USPC ................ 356/237.1–237.6, 238.1–238.3, 356/239.1–293.8, 240.1–241.6
See application file for complete search history.

(56) References Cited

U.S. PATENT DOCUMENTS

| | | | | |
|---|---|---|---|---|
| 1,943,510 A | * | 1/1934 | Bauersfeld | G02B 21/125 359/387 |
| 4,127,318 A | * | 11/1978 | Determann | G02B 21/082 359/387 |
| 4,441,124 A | * | 4/1984 | Heebner | G01N 21/94 250/559.41 |
| 4,585,315 A | * | 4/1986 | Sincerbox | G02B 21/125 359/387 |
| 4,881,802 A | * | 11/1989 | Stankewitz | G02B 21/084 359/387 |
| 5,580,162 A | * | 12/1996 | Murakami | G01N 21/8806 362/268 |
| 6,882,417 B2 | * | 4/2005 | Goldberg | G02B 21/0016 356/237.4 |
| 6,922,236 B2 | * | 7/2005 | Vaez-Iravani | G01N 21/47 356/237.2 |
| 7,049,155 B2 | * | 5/2006 | Reinhorn | G01N 21/8806 356/487 |

(Continued)

*Primary Examiner* — Gordon J Stock, Jr.
(74) *Attorney, Agent, or Firm* — Kilpatrick Townsend & Stockton LLP

(57) ABSTRACT

A system and method for multiple mode inspection of a sample. The system includes a radiation source, an objective lens, a bright field detection module, a dark field detection module and optics. The optics, when the system operates at a first mode, is configured to direct the input beam through a first opening, without substantially blocking any part of the input beam, towards a first region of the objective lens. The optics, when the system operates at a second mode, is configured to direct the input beam through a second opening, without substantially blocking any part of the input beam, towards a second region of the objective lens. The first region of the objective lens differs from the second region of the objective lens.

15 Claims, 21 Drawing Sheets

(56) References Cited

U.S. PATENT DOCUMENTS

| | | | |
|---|---|---|---|
| 7,271,889 B2* | 9/2007 | Cemic | G01N 21/8806 |
| | | | 356/237.2 |
| 8,891,079 B2 | 11/2014 | Zhao et al. | |
| 9,291,575 B2 | 3/2016 | Zhao et al. | |
| 9,354,212 B2* | 5/2016 | Berlatzky | G01N 33/00 |
| 9,772,297 B2* | 9/2017 | Nicolaides | G01N 21/9501 |
| 2007/0121106 A1* | 5/2007 | Shibata | G01N 21/8806 |
| | | | 356/237.2 |
| 2009/0059215 A1* | 3/2009 | Mehanian | G01N 21/8806 |
| | | | 356/237.2 |
| 2018/0329189 A1* | 11/2018 | Banna | G02B 21/0032 |

* cited by examiner

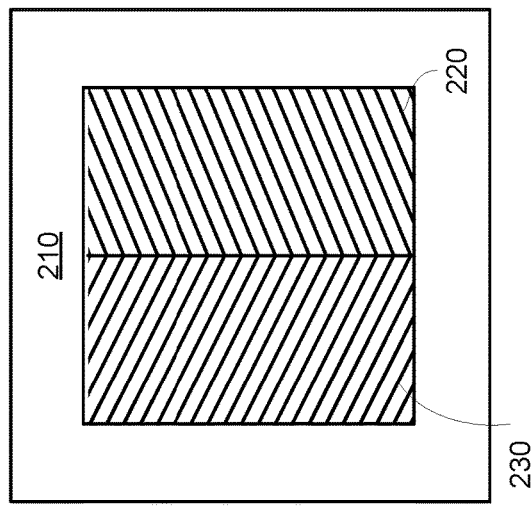
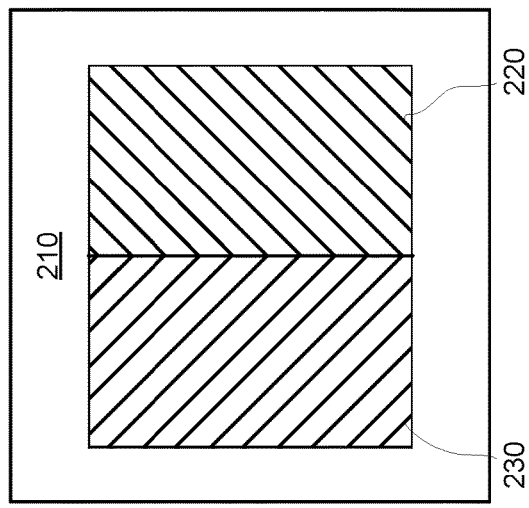
FIG. 19

SYSTEM AND METHOD FOR MULTIPLE MODE INSPECTION OF A SAMPLE

BACKGROUND OF THE INVENTION

Dark field inspection includes illuminating a sample and collecting scattered radiation while bright field inspection includes illuminating a sample and collecting reflected radiation.

These different inspection techniques may provide different information about different types of defects.

Different variations of dark field inspection and bright field inspection may involve illuminating the sample at different angles—also to provide different information about different types of defects.

Using totally different dark field optics and bright field optics may be too costly and complex.

There is a growing need to provide a system that may be cost effective, and may apply various variations of both dark field inspection and bright field inspection.

SUMMARY

There may be provided a system for multiple mode inspection of a sample, the system may include (i) a radiation source that may be configured to provide an input beam; (ii) an objective lens; (iii) a bright field detection module; (iv) a dark field detection module; and (v) optics that may be constructed and configured, when at a first mode, to direct the input beam towards a certain region of the objective lens. The objective lens may be configured to (a) focus the input beam directed towards the first region of the objective lens onto the sample at a first angle; (b) collect, by the objective lens a reflected beam that may be reflected from the object; (c) collect, by the objective lens, one or more scattered beams scattered from the sample, and (d) direct the reflected beam and the one or more scattered beams towards the optics. The the optics may be configured, when at the first mode, to direct the reflected beam towards the bright-field detection module and to direct the scattered beams towards the dark field detection module. The optics may be constructed and configured, when at a second mode, to direct the input beam towards another region of the objective lens; the other region of the objective lens differs from the certain region of the objective lens. The objective lens may be configured to (a) focus the input beam directed towards the other region of the objective lens onto the sample at a second angle; (b) collect, the reflected beam that may be reflected from the object; (c) collect, the one or more scattered beam scattered from the sample, and (d) direct the reflected beam and the one or more scattered beams towards the optics. The optics may be configured, when at the second mode, to direct the reflected beam towards the bright-field detection module and to direct the scattered beam towards the dark field detection module. The first angle differs from the second angle. Each one of the first angle and the second angle may be normal or non-normal.

The certain region of the objective lens and the other region of the objective lens may be located at any location of the objective lens. Examples of the certain region and of the other region may be illustrated in FIG. 20.

There may be provided a system for multiple mode inspection of a sample, the system may include a radiation source that may be configured to provide an input beam, an objective lens, a bright field detection module, a dark field detection module, and optics. The optics, when the system operates at a first mode, may be configured to direct the input beam through a first opening, without substantially blocking any part of the input beam, towards a first region of the objective lens. The optics, when the system operates at a second mode, may be configured to direct the input beam through a second opening, without substantially blocking any part of the input beam, towards a second region of the objective lens; wherein the first region of the objective lens differs from the second region of the objective lens. The objective lens may be configured to: (a) focus the input beam directed towards the first region of the objective lens onto the sample at a first angle; (b) focus the input beam directed towards the second region of the objective lens onto the sample at a second angle; wherein the first angle differs from the second angle; (c) collect a reflected beam that may be reflected from the object; (d) collect one or more scattered beams scattered from the object; (e) direct the reflected beam and the one or more scattered beams towards the optics. The optics may be configured to direct the reflected beam towards the bright field detection module, and to direct the one or more scattered beam towards the dark field detection module.

The first angle may be normal to the sample and the second angle may be an oblique angle.

When the system operates in the first mode, the objective lens may be configured to collect the reflected beam at the first region of the objective lens, and to collect the one or more scattered beam at one or more regions of the objective lens that differ from the first region of the objective beam.

When the system operates in the second mode, the objective lens may be configured to collect a scattered beam of the one or more reflected beams at the first region of the objective lens, and to collect the reflected beam at a region of the objective lens that differs from the first region of the objective beam.

The system may include a telescope, wherein the objective lens may be positioned between the sample and the telescope.

The telescope may include multiple lenses; wherein at least two lenses may be aspheric lenses.

The system may include a mechanical manipulator that may be configured to change a location of at least one optical components of the optics between the first mode and the second mode. The mechanical manipulator may include a motor and a gear or any other known mechanical components and may be configured to perform any movement—including any linear or rotational movement along any axis.

The first opening may be formed in a first mask. The second opening may be formed in a second mask. The mechanical manipulator may be configured to change positions of the first mask and of the second mask between the first mode and the second mode.

The optics may include at least two movable reflecting mirrors that may be movable between the first mode and the second mode.

The optics may include a pair of prisms and a blocking element that may be positioned between the pair of prisms.

The optics may include a polarization control unit for controlling a polarization of the input beam.

The system may include a polarizer that precedes the dark field detection module. The polarizer may include a first segment and a second segments. The first segment may include a first grid of parallel metallic segments. The second segment may include a second grid of parallel metallic segments. The first grid may be oriented to the second grid.

The system wherein the optics may include a path compensation unit for compensating for an optical path difference between the first mode and the second mode.

There may be provided a method for multiple mode inspection of a sample by a system, the method may include: providing an input beam, by a radiation source of the system; directing by optics of the system, when the system operates at a first mode, the input beam through a first opening, without substantially blocking any part of the input beam, towards a first region of the objective lens; focusing, by an objective lens of the system, when the system operates at the first mode, the input beam directed towards the first region of the objective lens onto the sample at a first angle; directing by the optics, when the system operates at a second mode, the input beam through a second opening, without substantially blocking any part of the input beam, towards a second region of the objective lens; wherein the first region of the objective lens differs from the second region of the objective lens; focusing, by the objective lens, when the system operates at the second mode, the input beam directed towards the first region of the objective lens onto the sample at a second angle; wherein the first angle differs from the second angle; collecting, by the objective lens, when the system operates in the first mode and when the system operates in the second mode, a reflected beam that may be reflected from the object; collecting, by the objective lens, when the system operates in the first mode and when the system operates in the second mode, one or more scattered beams that may be scattered from the object; directing the reflected beam and the one or more scattered beams towards the optics; directing, by the optics, the reflected beam towards a bright field detection module; and directing, by the optics, the one or more scattered beam towards a dark field detection module.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 19 illustrates an example of a polarizer.

DETAILED DESCRIPTION OF THE DRAWINGS

Figure 1:
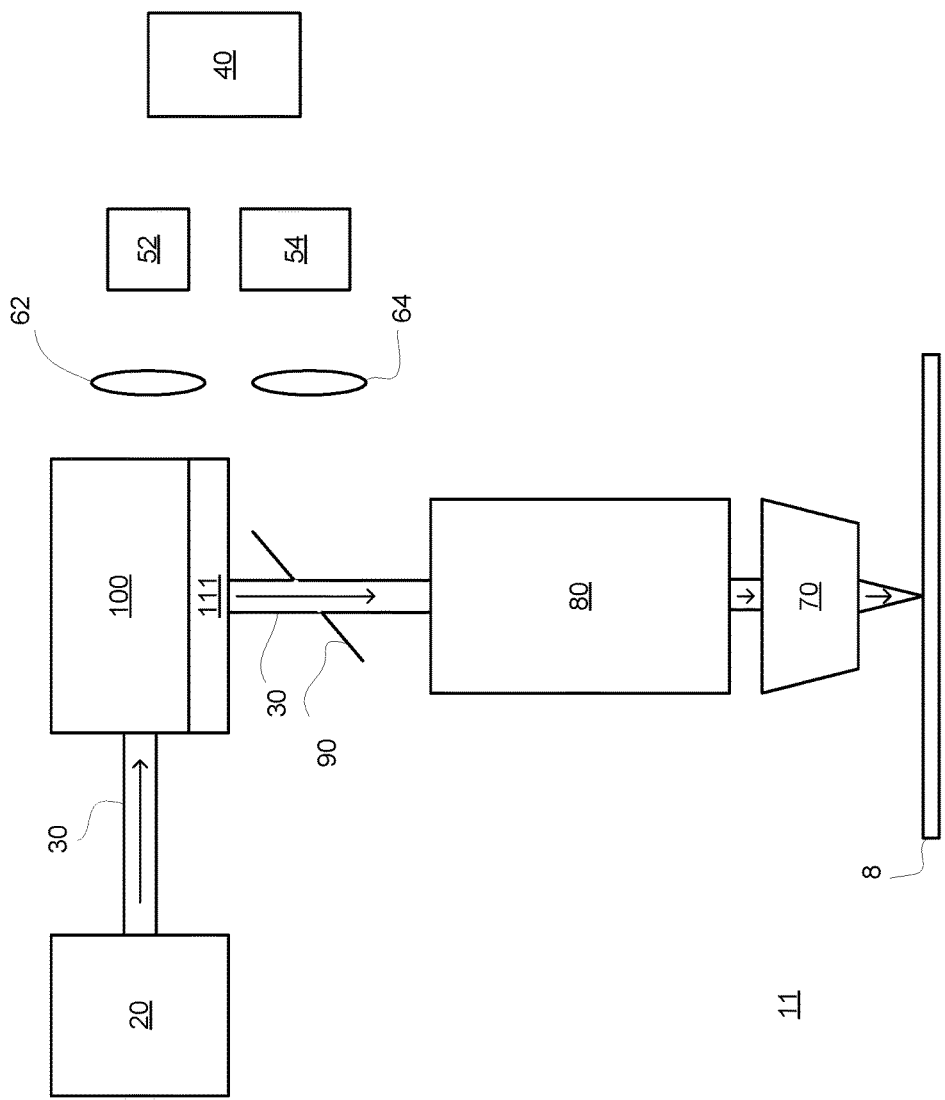
FIG. 1 illustrates an example of a system and a sample.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method.

Any reference in the specification to a system should be applied mutatis mutandis to a method that may be executed by the system.

There may be provided a system and method for inspecting a sample in multiple modes. The system may have optics that may operate in at least two modes that differ from each other by the illumination angle of a radiation beam.

In both modes the system may perform both dark field inspection and bright field inspection. Due to the difference of the illumination angle the system (a) applies a first variant of bright field inspection and a first variant of dark field inspection when operating at a first mode, and (b) applies a second variant of bright field inspection and a second variant of dark field inspection when operating at a second mode.

The system includes optics and an objective lens that are used in both modes, although the optics are configured in different manners when the system operates at different modes.

The optics changes the illumination path and the collection path of the system without substantially blocking the input beam—therefore exhibiting a higher energy efficiency and better sensitivity in comparison to systems that block substantial parts of the input beam at the illumination path.

The system may pass the input beam through a first aperture when operating in the first mode. The first aperture may be formed in a first mask. The first mask may be a beam splitter. The mask may be a mirror with one or more apertures. The system may pass the input beam through a second aperture when operating in the second mode. The second aperture may be formed in a second mask. The second mask may be a beam splitter. The second mask may differ from the first mask.

The second aperture and the first aperture are located at different positions in relation to the objective lens.

Operating the system at different modes may require to change the configuration of the optics—but may not require displacements of other parts of the system—such as but not limited to a radiation source, a telescope, an objective lens, a control unit, a bright field detection module, and a dark field detection module. Furthermore—the radiation source may direct the input beam to the same location—in both modes.

Illuminating different regions of the objective lens will cause the objective lens to illuminate the sample at different angles—allowing the system to apply different variants of bright field inspection and dark field inspection.

FIGS. 1-19 illustrates (a) a first mode of operation during which a center region of the objective lens is illuminated and a sample that is illuminated at a normal angle, and (b) a second mode of operation during which an out-of-center region of the objective lens is illuminated and the sample that is illuminated at an oblique angle.

It should be noted that these are merely non-limiting example of illuminations—and that different modes of operation may illuminate any different regions of the objective lens—and thus the sample may be illuminated at virtually almost any angle. It should be noted that different modes of operation may also change the manner in which the scattered beam is collected and/or the reflected beam is collected.

Figure 2:
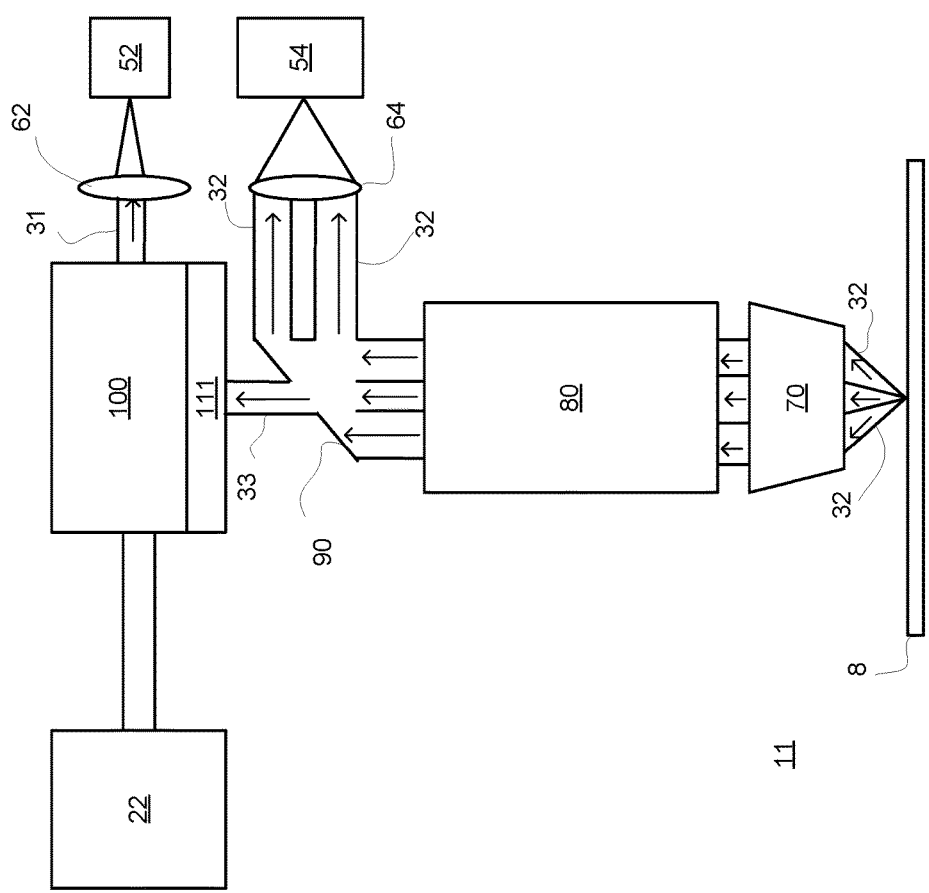
FIG. 2 illustrates an example of a system and a sample.

FIGS. 1 and 2 are examples of system 11 when operating at a first mode. FIG. 1 illustrates an illumination path and FIG. 2 illustrates a collection path.

System 11 includes (a) a radiation source 20 that is configured to provide an input beam 30, (b) an objective lens 70, (c) a bright field detection module that includes bright field lens 62 and bright field detector 52, (d) a dark field detection module that includes dark field lens 64 and dark field detector 54, (e) telescope 80, (f) polarization control unit 111, (g) first mask 90, (h) image processor 40, (i) optics 100, and a controller (not shown).

Image processor 40 is configured to process the detection signals from the bright field detection module and from the dark field field detection module. The processing may include applying any inspection algorithm such as did to die comparison, die to reference comparison, cell to cell comparison, and the like.

System 11 may also include parts (not shown) such as a storage unit, a mechanical module for supporting and moving the sample, and the like.

When system 11 operates at the first mode, optics 100 may be configured to receive the input beam 30, direct the input beam 30 through a first opening of first mask 90 so that the entire input beam (or almost all of the input beam) passes through the first opening—without blocking substantial parts of the input beam—thereby reducing energy losses and increasing the sensitivity of the system.

It should be noted that before passing through the first opening—the polarization of the input beam may be set by the polarization control unit 111.

The input beam 30 passes through a center region of the telescope 80, passes through a center region of the objective lens 70, and finally is focused by the center region of the objective lens on the sample 8 at a normal angle.

A reflected beam 33 is reflected from the sample 8, collected by the center region of the objective lens 70, directed towards a center region of the telescope 80, passes through the center region of the telescope 80, passes through the first opening of the first mask 90, passes through the polarization control unit 111, and is directed by optics 100 towards the bright field lens 62 that focuses the reflected beam onto the bright field detector 52.

A scattered beam 32 is scattered from the sample 8, collected by an out-of-center region of the objective lens 70, directed towards an out-of-center region of the telescope 80, passes through the out-of-center region of the telescope 80, reflected by a backside reflecting region of first mask 90 towards the dark field lens 64, and is focused, by the dark field lens onto the dark field detector 54.

Figure 3:
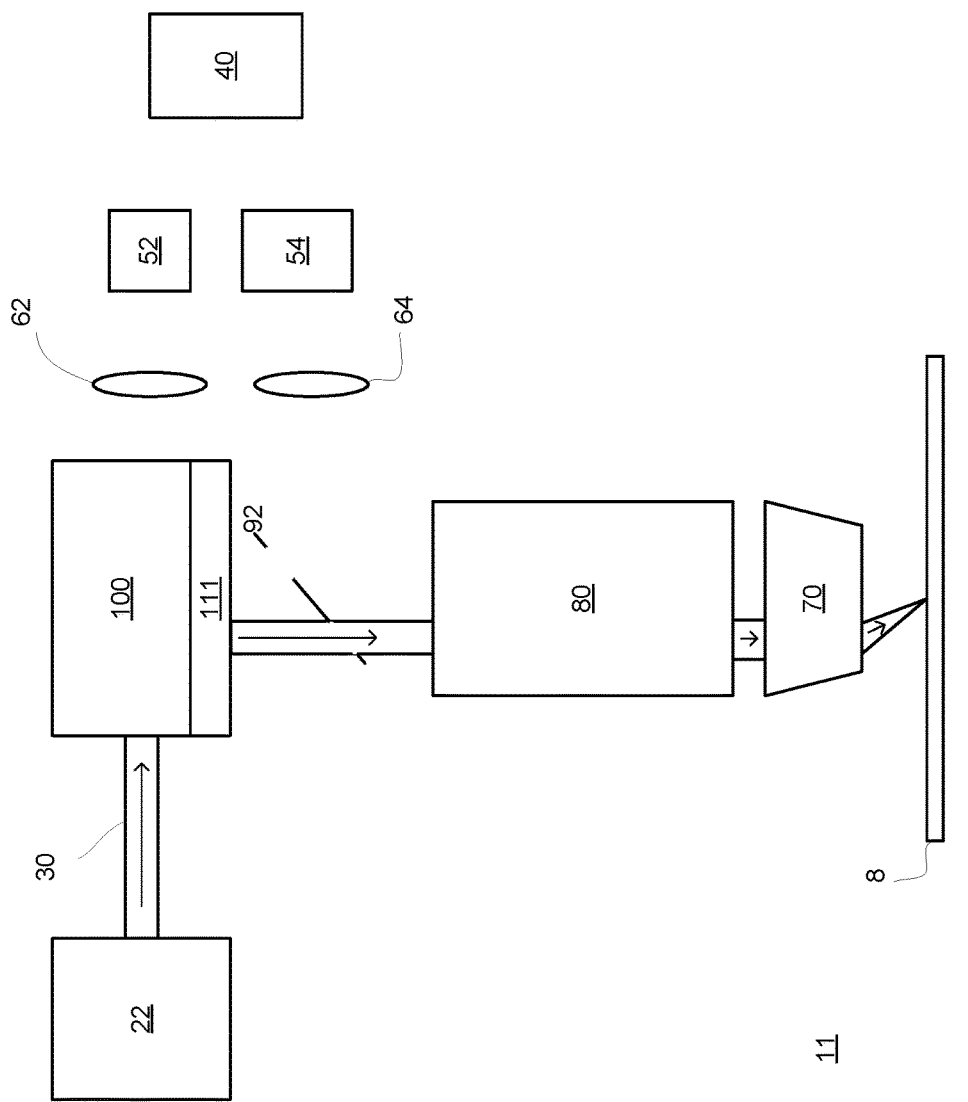
FIG. 3 illustrates an example of a system and a sample.
Figure 4:
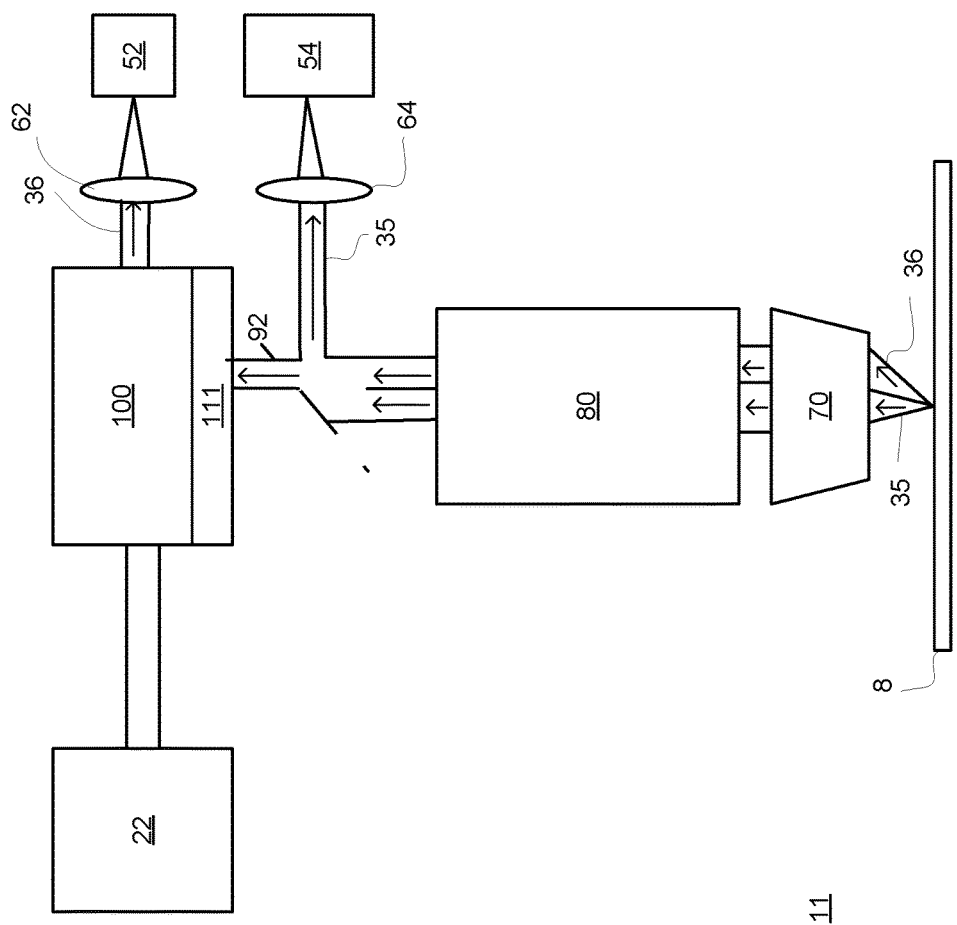
FIG. 4 illustrates an example of a system and a sample.

FIGS. 3 and 4 are examples of system 11 when operating at a second mode. FIG. 3 illustrates an illumination path and FIG. 4 illustrates a collection path.

When the system 11 operates at the second mode, optics 100 may be configured to receive the input beam 30, direct the input beam 30 through a second opening that is formed in the second mask 92 so that the entire input beam (or almost all of the input beam) passes through the second opening—without blocking substantial parts of the input beam—thereby reducing energy losses and increasing the sensitivity of the system.

It should be noted that before passing through the second opening—the polarization of the input beam may be set by the polarization control unit 111.

The input beam 30 passes through an out-of-center region of the telescope 80, passes through an out-of-center region of the objective lens 70, and finally is focused by the out-of-center region of the objective lens on the sample 8 at an oblique angle.

A reflected beam 36 is reflected from the sample 8, collected by another out-of-center region of the objective lens 70, directed towards another out-of-center region of the telescope 80, passes through the other out-of-center region of the telescope, passes through a third opening formed in the second mask 92, passes through the polarization control unit 111, and is directed by optics 100 towards the bright field lens 62 that focuses the reflected beam onto the bright field detector 52.

A scattered beam 35 is scattered from the sample 8, is collected by the center region of the objective lens 70, directed towards the center region of the telescope 80, passes through the center region of the telescope 80, reflected by a backside reflecting region of third mask 94 towards the dark field lens 64, and is focused, by the dark field lens onto the dark field detector 54.

The center region, the out-of-center region and the other out-of-center region may not overlap or may partially overlap.

Figure 5:
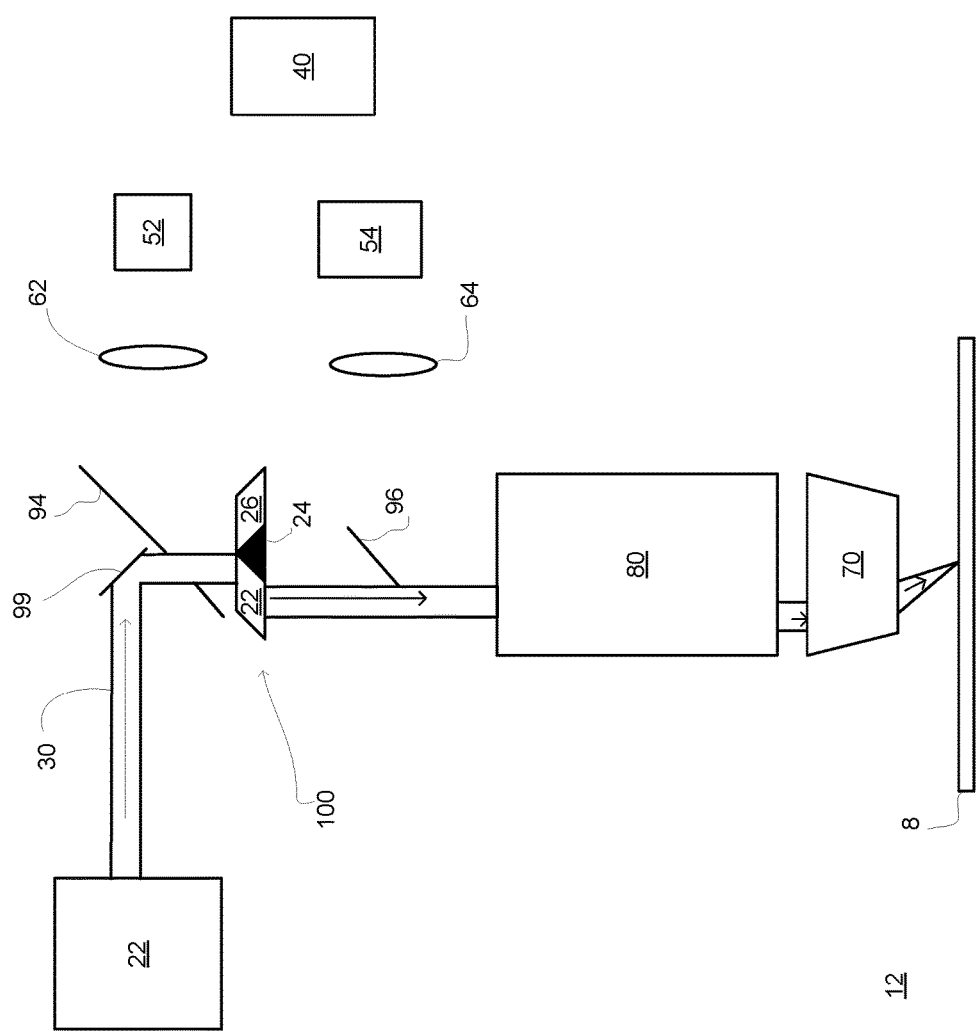
FIG. 5 illustrates an example of a system and a sample.
Figure 6:
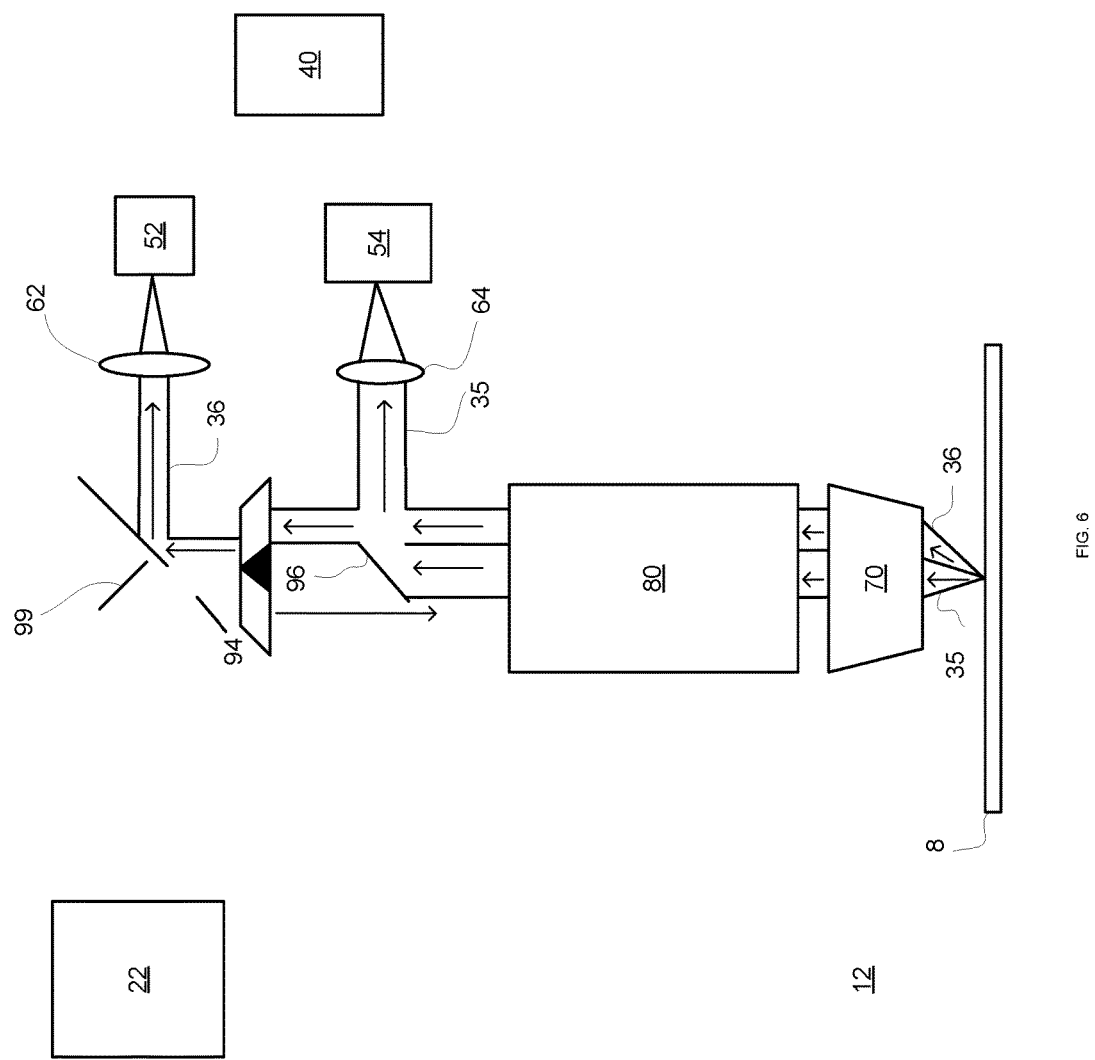
FIG. 6 illustrates an example of a system and a sample.

FIGS. 5 and 6 are examples of system 12 when operating at a second mode. FIG. 5 illustrates an illumination path and FIG. 6 illustrates a collection path.

In FIGS. 5 and 6 the optics 100 include upper reflector 99, third mask 94, first prism 22, second prism 26, blocking element 24 and a lower reflector 96.

The upper reflector 99 directs the input beam 30 through an opening of third mask 94 so that the entire input beam (or almost all of the input beam) passes through the first opening—without blocking substantial parts of the input beam—thereby reducing energy losses and increasing the sensitivity of the system.

The first prism 22 is configured to receive the input beam that passes through the aperture—and divert the input beam 30 away from the center of the blocking element 24—and away from the center region of the telescope 80. The input beam 30 then passes through an out-of-center region of the telescope 80, passes through an out-of-center region of the objective lens 70, and finally is focused by the out-of-center region of the objective lens on the sample 8 at an oblique angle.

A reflected beam 36 is reflected from the sample 8, collected by another out-of-center region of the objective lens 70, directed towards another out-of-center region of the telescope 80, passes through the other out-of-center region of the telescope, is deflected by the second prism 26 towards the center of the blocking element 24, and is reflected by a backside reflecting region of the third mask 94 towards the bright field lens 62 that focuses the reflected beam onto the bright field detector 52.

The second prism 26 is configured to divert the reflected beam—so that the reflected beam may be reflected by the backside reflecting region of the third mask 94 towards the the same region of the bright field lens 62 that receives the reflected light when the system operates at the first mode.

When operating at the first mode the first prism 22, the blocking element 24, the second prism 26 and the lower reflector are moved from the path of the input beam.

A scattered beam 35 is scattered from the sample 8, is collected by the center region of the objective lens 70, directed towards the center region of the telescope 80, passes through the center region of the telescope 80, reflected by the lower reflector 96 towards the dark field lens 64, and is focused, by the dark field lens onto the dark field detector 54.

Figure 7:
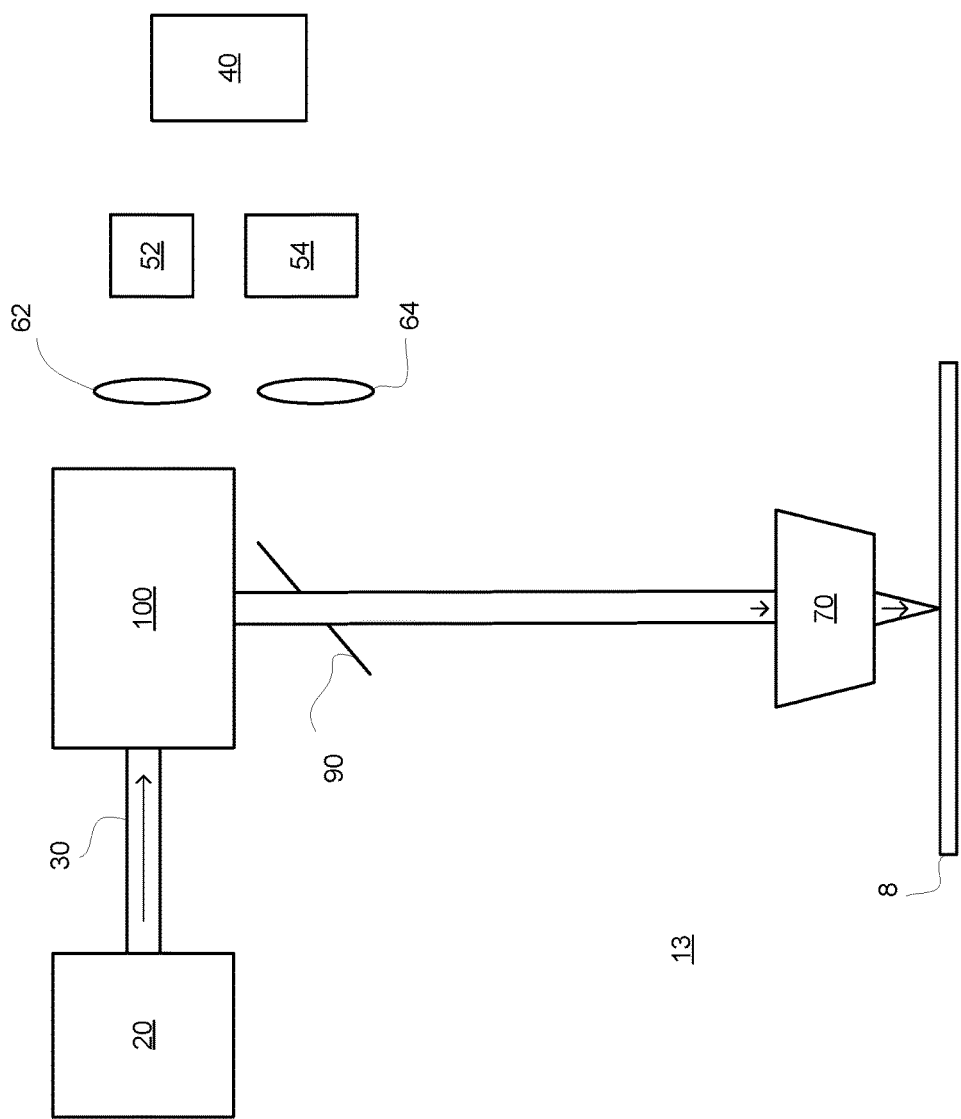
FIG. 7 illustrates an example of a system and a sample.
Figure 8:
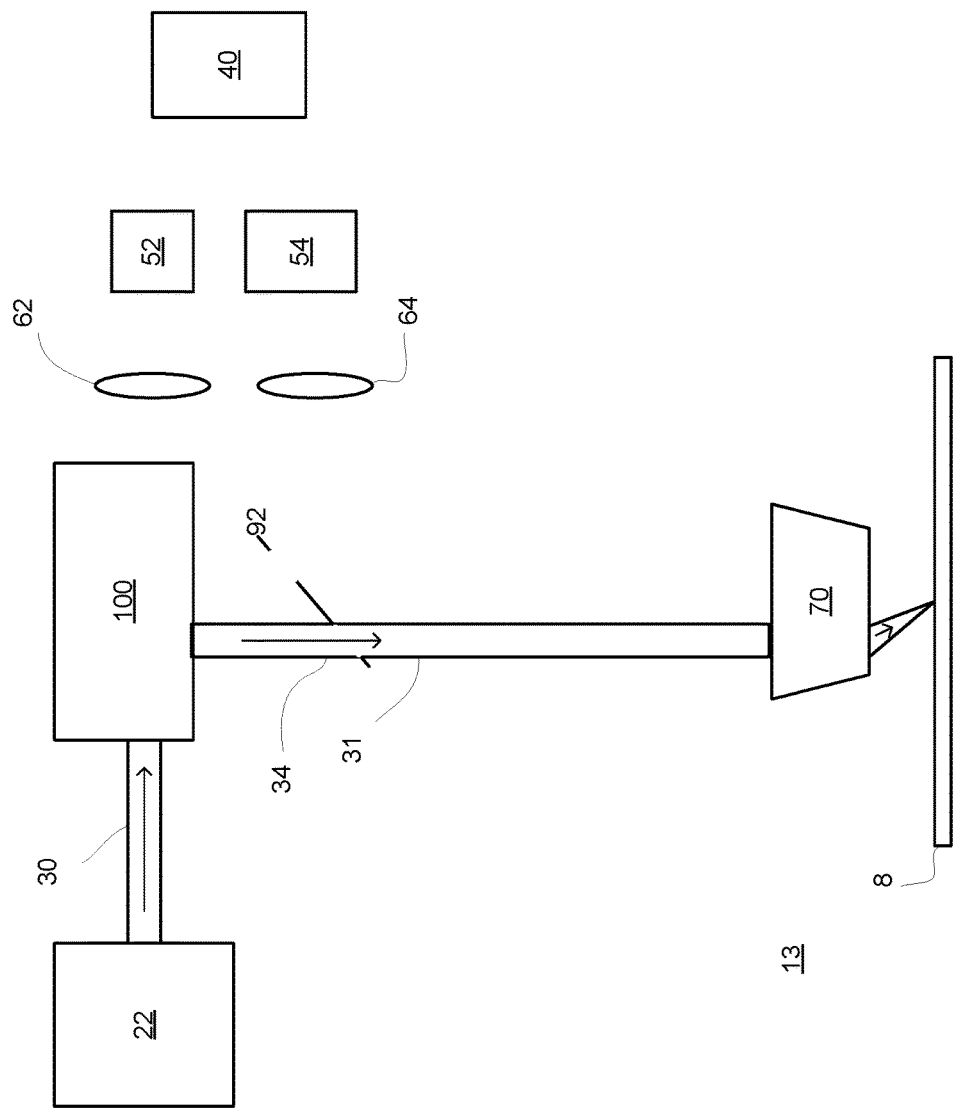
FIG. 8 illustrates an example of a system and a sample.

FIGS. 7 and 8 illustrate system 13 that differs from system 11 by not having a telescope.

Figure 9:
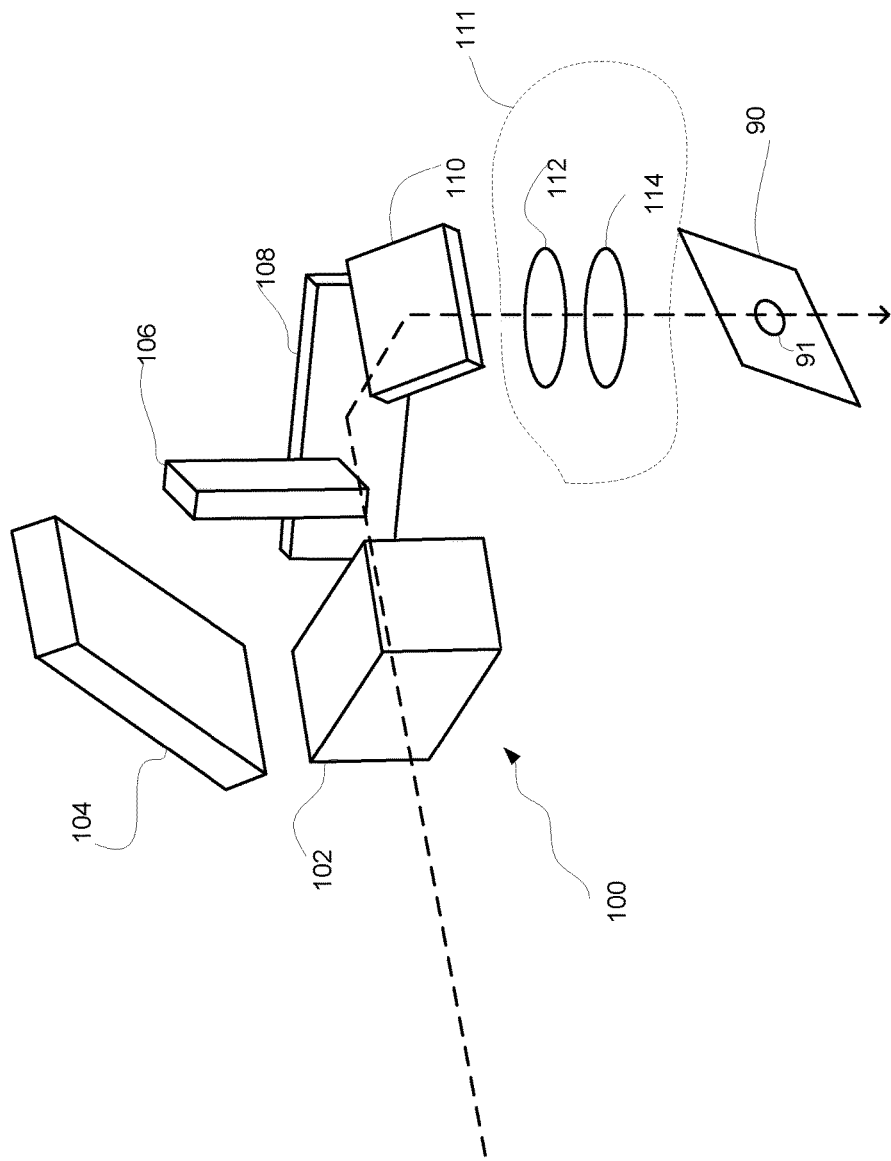
FIG. 9 illustrates an example of some optical components of the system.
Figure 10:
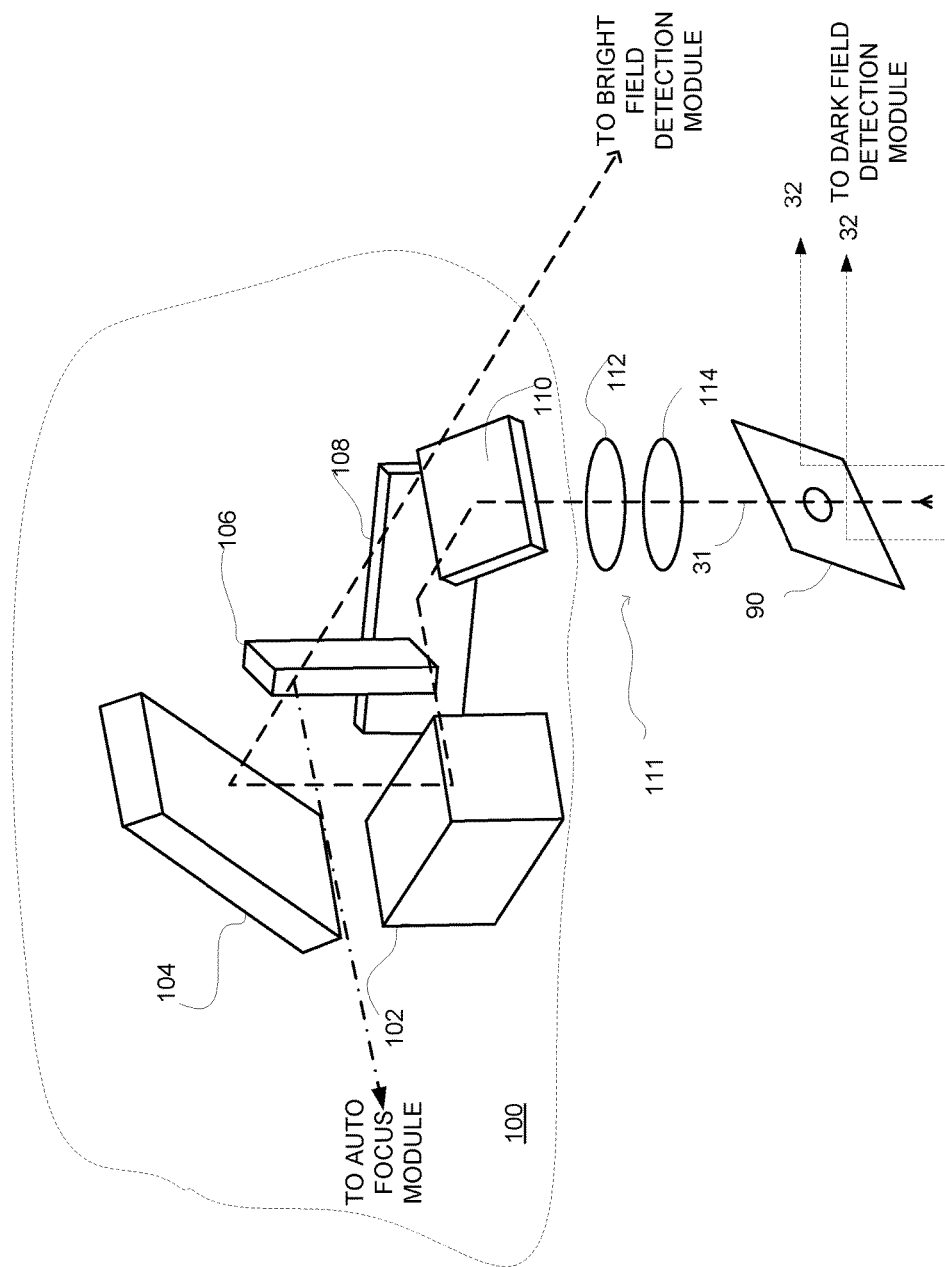
FIG. 10 illustrates an example of some optical components of the system.

FIGS. 9 and 10 illustrates optics 100, polarization control unit 111 and first mask when the system operates at a first mode. FIG. 9 illustrates an illumination path and FIG. 10 illustrates a collection path.

Optics 100 includes first beam splitter 102, second beam splitter 106, first reflector 108, second reflector 110 and third reflector 104.

Polarization control unit 111 include half wavelength retarder 112 and one fourth wavelength retarder 114.

In FIGS. 9 and 10 first reflector 108 and second reflector 110 are positioned at a first position.

Input beam 30 passes through first beam splitter 102, is reflected by first reflector 108 towards second reflector 110, is reflected by second reflector 110 towards polarization control unit 111, passes through polarization control unit 111, and passes through the first aperture 91 of first mask 90—without substantially blocking any part of the input beam.

In FIG. 10 scattered beam 32 is reflected by a backside reflecting region of first mask 90 towards dark field detection module (not shown).

The reflected beam 32 passes through the first opening, through the polarization control unit 111, is reflected by second reflector 110 towards first reflector 108, is reflected by first reflector 108 towards first beam splitter 102, is reflected by first beam splitter 102 towards third reflector 104, is reflected by third reflector 104 towards second beam splitter 106 and is split to a main signal that propagates towards the bright field detection module (not shown) and a secondary signal that is sent to an auto-focus module (not shown).

Figure 11:
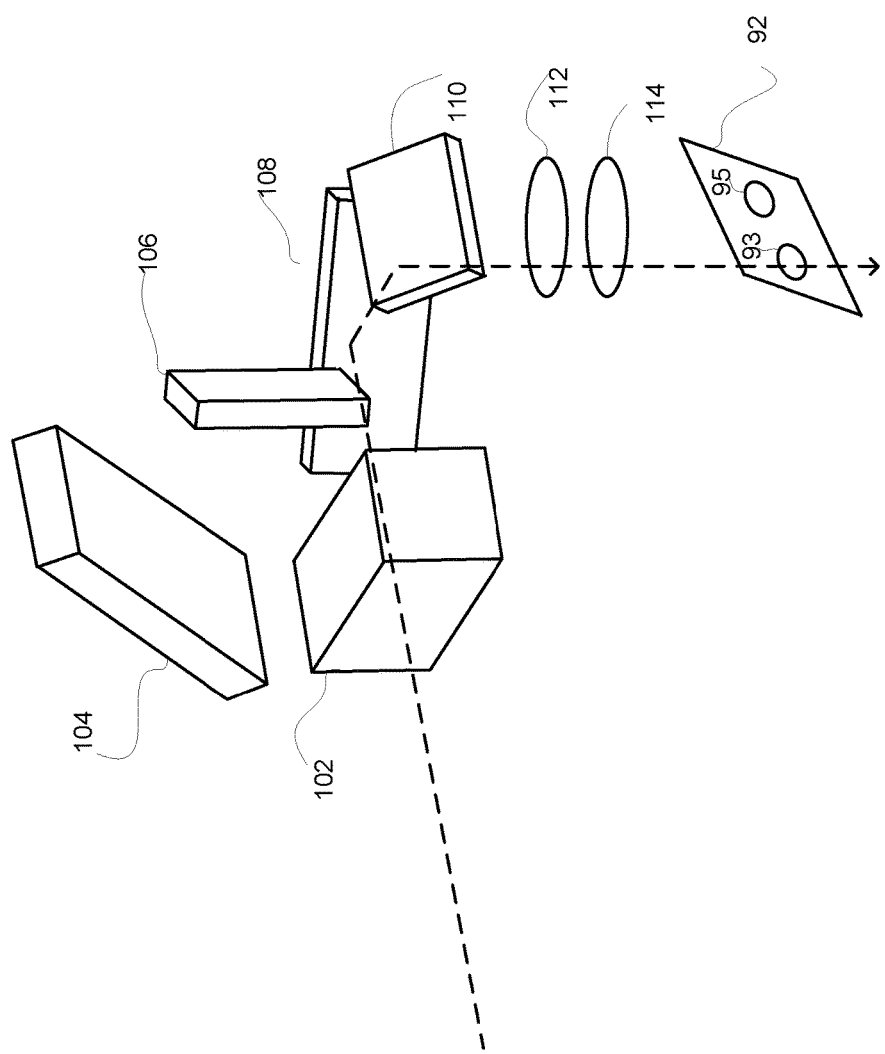
FIG. 11 illustrates an example of some optical components of the system.
Figure 12:
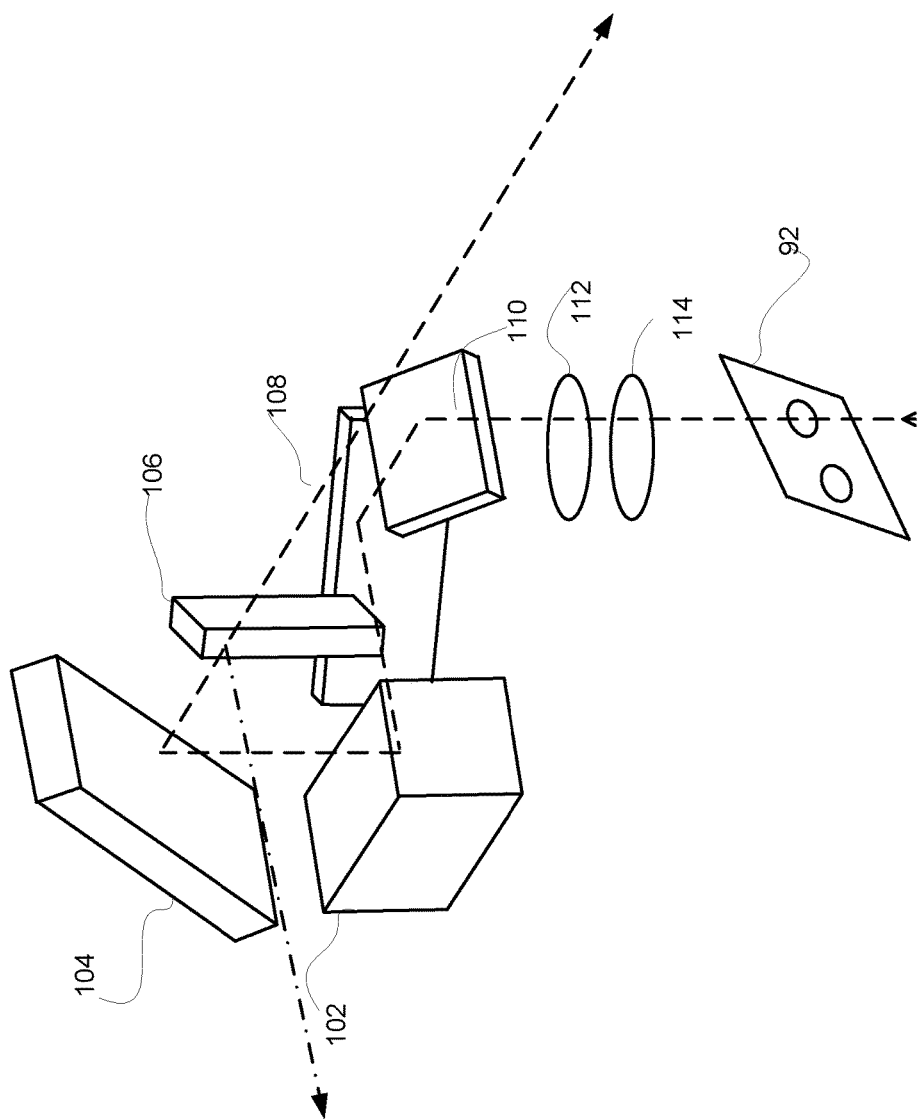
FIG. 12 illustrates an example of some optical components of the system.
Figure 13:
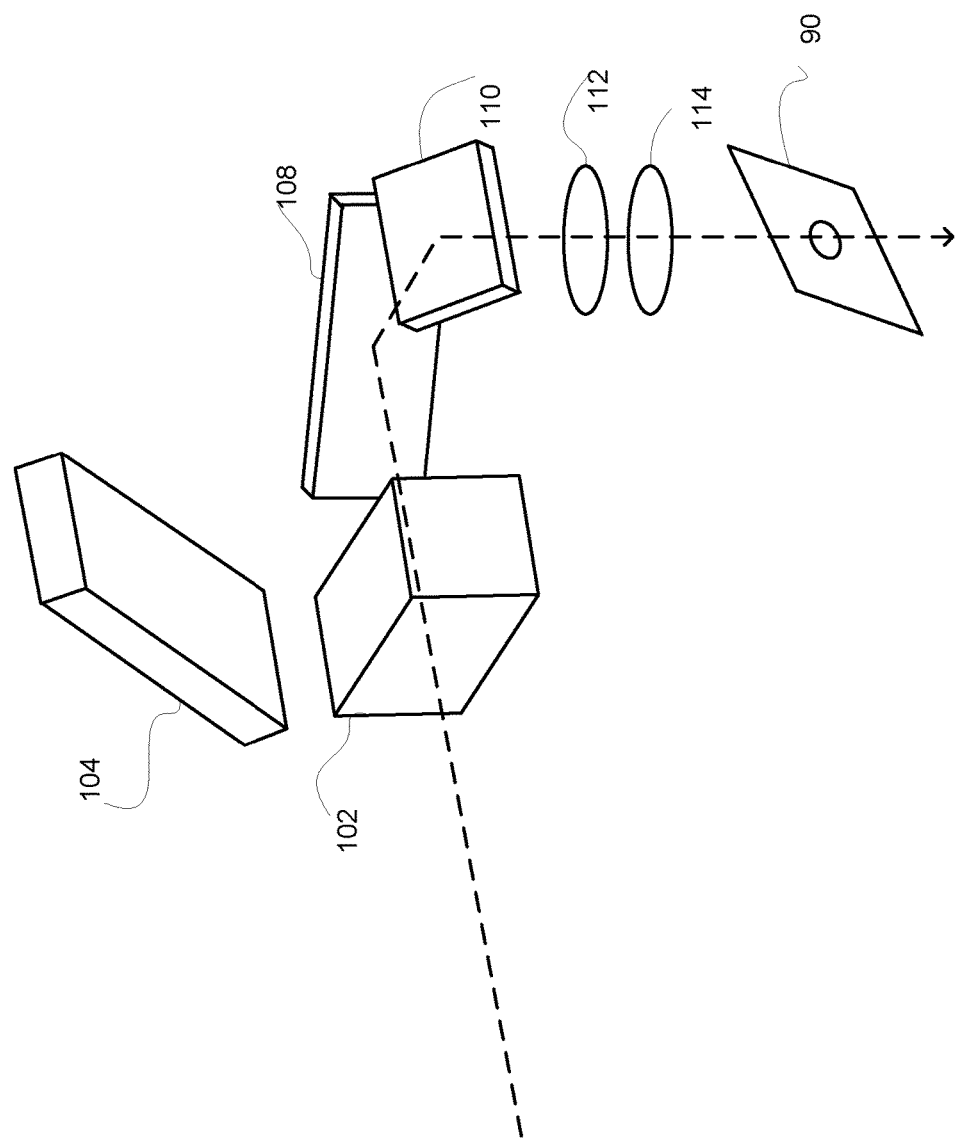
FIG. 13 illustrates an example of some optical components of the system.
Figure 14:
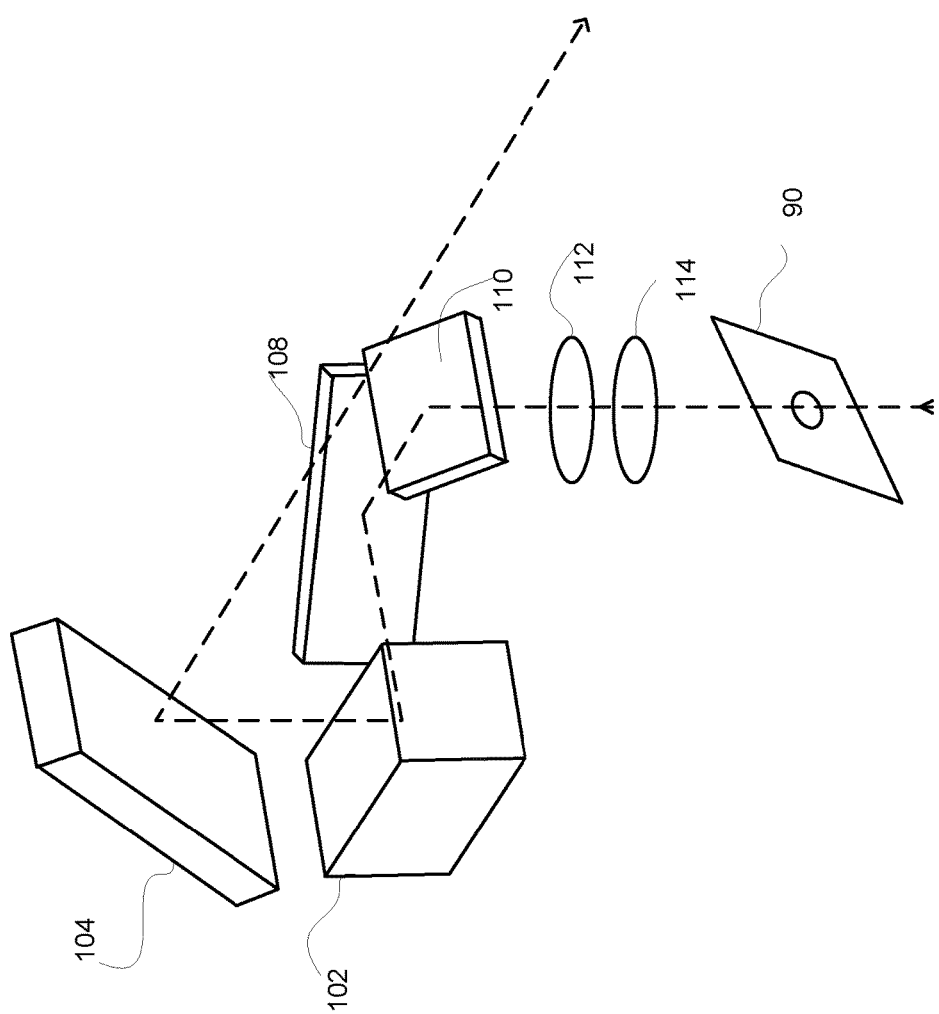
FIG. 14 illustrates an example of some optical components of the system.
Figure 15:
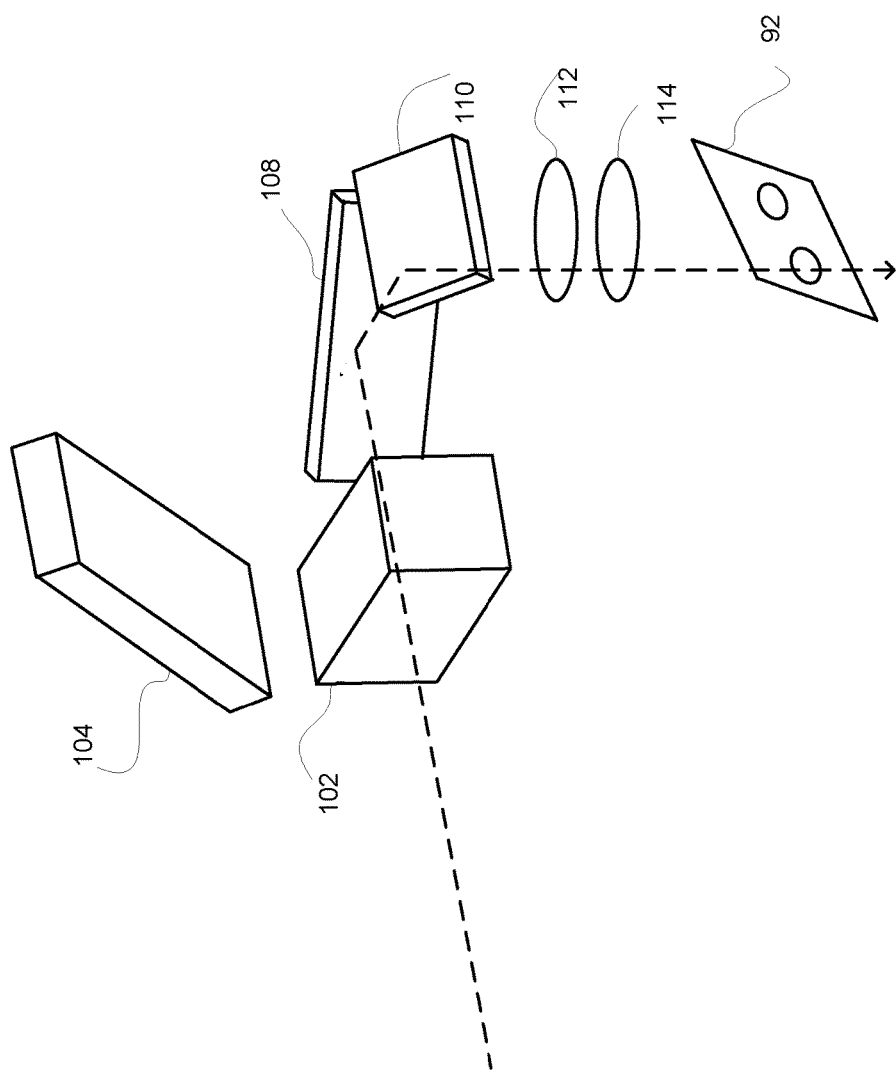
FIG. 15 illustrates an example of some optical components of the system.
Figure 16:
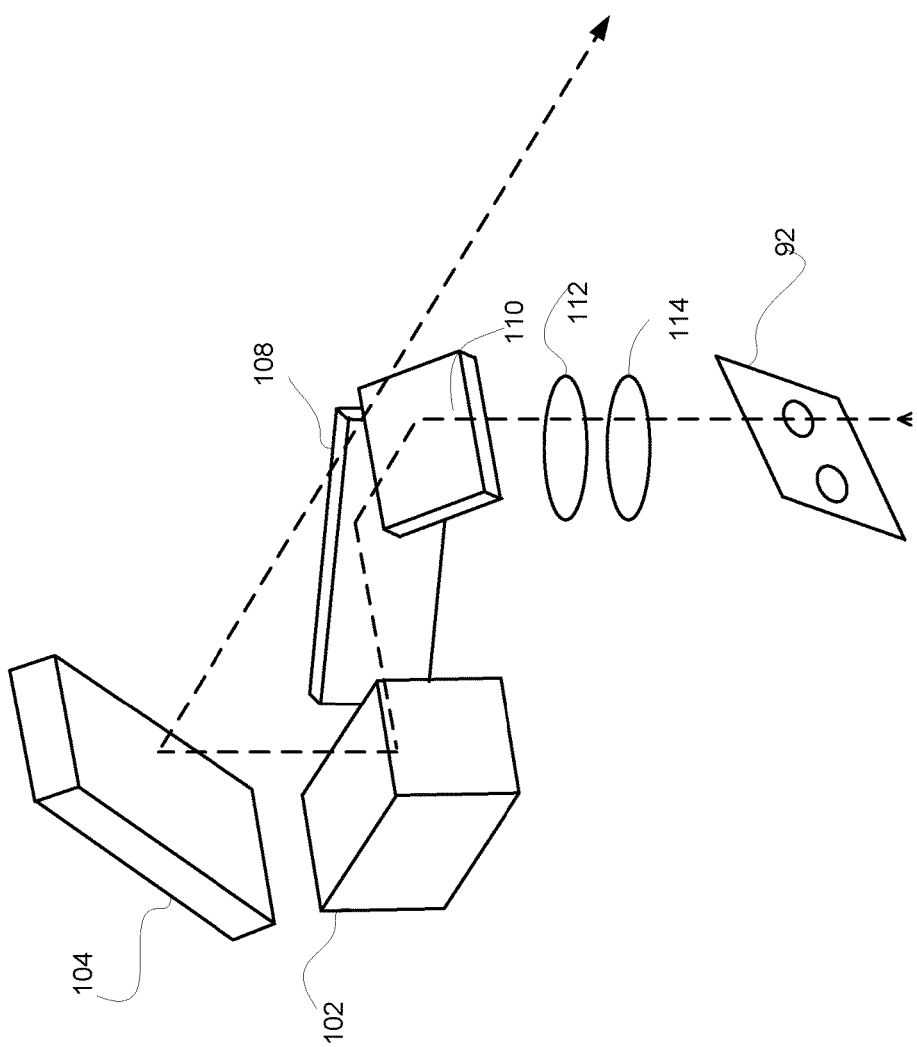
FIG. 16 illustrates an example of some optical components of the system.

FIGS. 11 and 12 illustrates optics 100, polarization control unit 111 and first mask when the system operates at a second mode. FIG. 11 illustrates an illumination path and FIG. 12 illustrates a collection path.

Optics 100 includes first beam splitter 102, second beam splitter 105, first reflector 108, second reflector 110 and third reflector 104.

Polarization control unit 111 include half wavelength retarder 112 and one fourth wavelength retarder 114.

In FIGS. 11 and 12 first reflector 108 and second reflector 110 are positioned at a second position that differs from the first position.

Input beam 30 passes through first beam splitter 102, is reflected by first reflector 108 towards second reflector 110, is reflected by second reflector 110 towards polarization control unit 111, passes through polarization control unit 111, and passes through the second aperture 93 formed in second mask 92—without substantially blocking any part of the input beam.

In FIG. 12 scattered beam 32 is reflected by a backside reflecting region of second mask 92 towards dark field detection module (not shown).

The reflected beam 36 passes through a third opening 95 formed in second mask 92, through the polarization control unit 111, is reflected by second reflector 110 towards first reflector 108, is reflected by first reflector 108 towards first beam splitter 102, is reflected by first beam splitter 102 towards third reflector 104, is reflected by third reflector 104 towards second beam splitter 106 and is split to a main signal that propagates towards the bright field detection module (not shown) and a secondary signal that is sent to an auto-focus module (not shown).

FIGS. 13-16 differ from FIGS. 9-12 by having optics 100 without second beam splitter 106. In these optics 100—the third reflector 104 reflects the reflected beam towards the bright field detection module (not shown).

First reflector 108 and second reflector 110 are movable reflecting mirrors.

Figure 17:
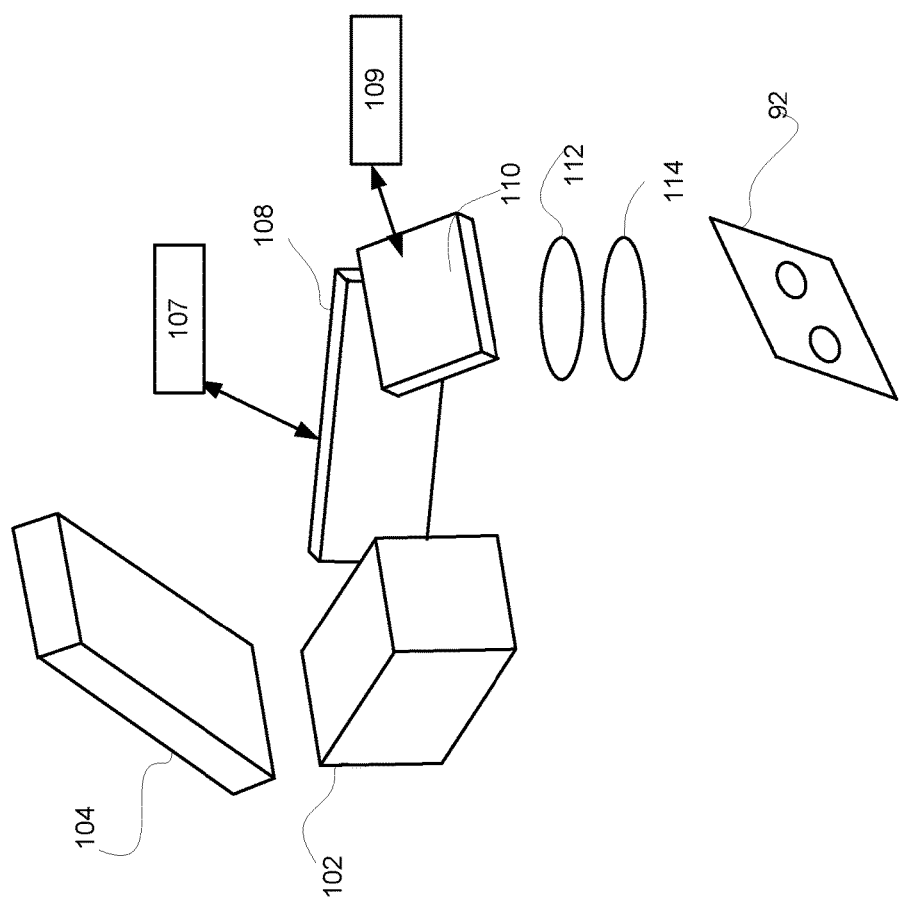
FIG. 17 illustrates an example of some optical components of the system.

FIG. 17 illustrates a first mechanical manipulator 107 for changing the position of first reflector 108 between the first position and the second position. The second mechanical manipulator 109 is for changing the position of the second reflector 110 between the first position and the second position.

Polarizing the scattered beam may include the sensitivity of the system to various defects. Introducing a polarizer before the dark field detection module may improve the sensitivity of the system. The polarizer may be static or may be moved—in the path of the reflected beam, out the path of the reflected beam, may be moved (for example rotated) while in the path of the reflected beam—to change the polarized components of the reflected beam that reach the dark field detection module.

Figure 18:
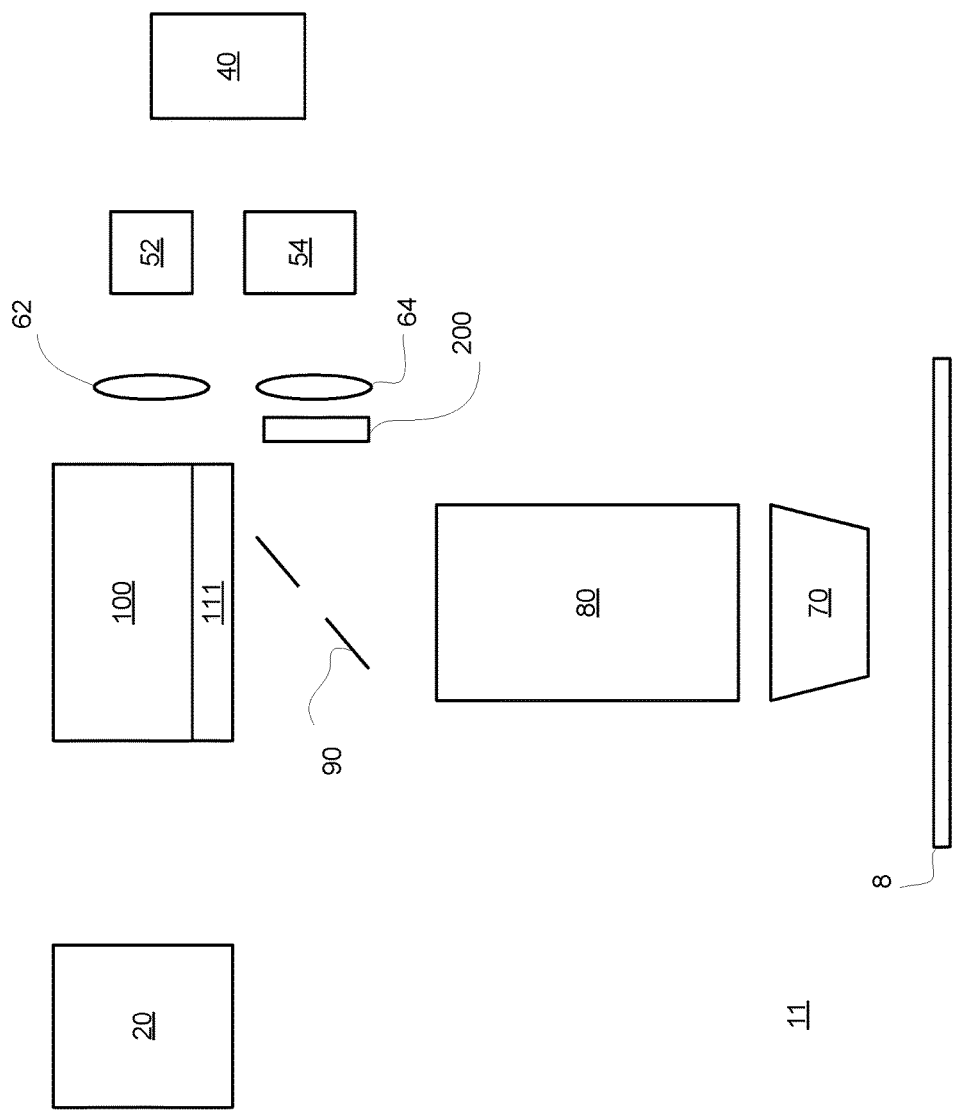
FIG. 18 illustrates an example of a system and a sample.

FIG. 18 illustrates an example of system 11 that includes a polarizer 200 that is positioned between the first mask 90 and the dark field lens 64. The polarizer may be included in any other system illustrated in any of the figures. The polarizer 200 may receive all the scattered light collected by the objective lens. The polarizer 200 may be positioned between the dark field detection module and the first mask.

The polarizer is compact, based on grids of metallic segments, the system may replace between polarizers with differently oriented grids of metallic segments in a simple manner, the polarizer is more compact than a polarizing beam splitter and insensitive (relative to a cube like polarizer) to AOI.

FIG. 19 illustrates an example of polarizer 200. Polarizer 200 includes a frame 210, a first segment 220 for polarizing a first segment of the scattered beam, and a second segments 230 for polarizing a first segment of the scattered beam.

The first segment 220 may include a first grid of parallel metallic segments. The second segment 230 may include a second grid of parallel metallic segments.

The metallic segments may have sub-micron dimensions—especially smaller than a wavelength of the radiation.

The first grid is oriented to the second grid.

FIG. 19 illustrates two polarizers that differ from each other by the orientation of the grids. In the left polarizer the first grid is oriented at plus forty five degrees and the second grid is oriented at minus forty five degrees. In the right polarizer the first grid is oriented at plus thirty degrees and the second grid is oriented at minus thirty degrees. Other orientations may be provided.

It should be noted that any one of the mentioned above systems may introduce a tilt between the sample and various parts of system (objective lens, telescope, optics, masks, and the like). This tilt will change the regions of the objective lens that will receive scattered beams and/or reflected beams.

The system may include a path compensation unit for compensating for path differences resulting from working in the different modes. The path compensation unit may include, for example, a glass block or a glass optical component—or any optical element that a has a transmission index that differs from a transmission index of air. Any other path compensation unit may be provided.

Figure 20:
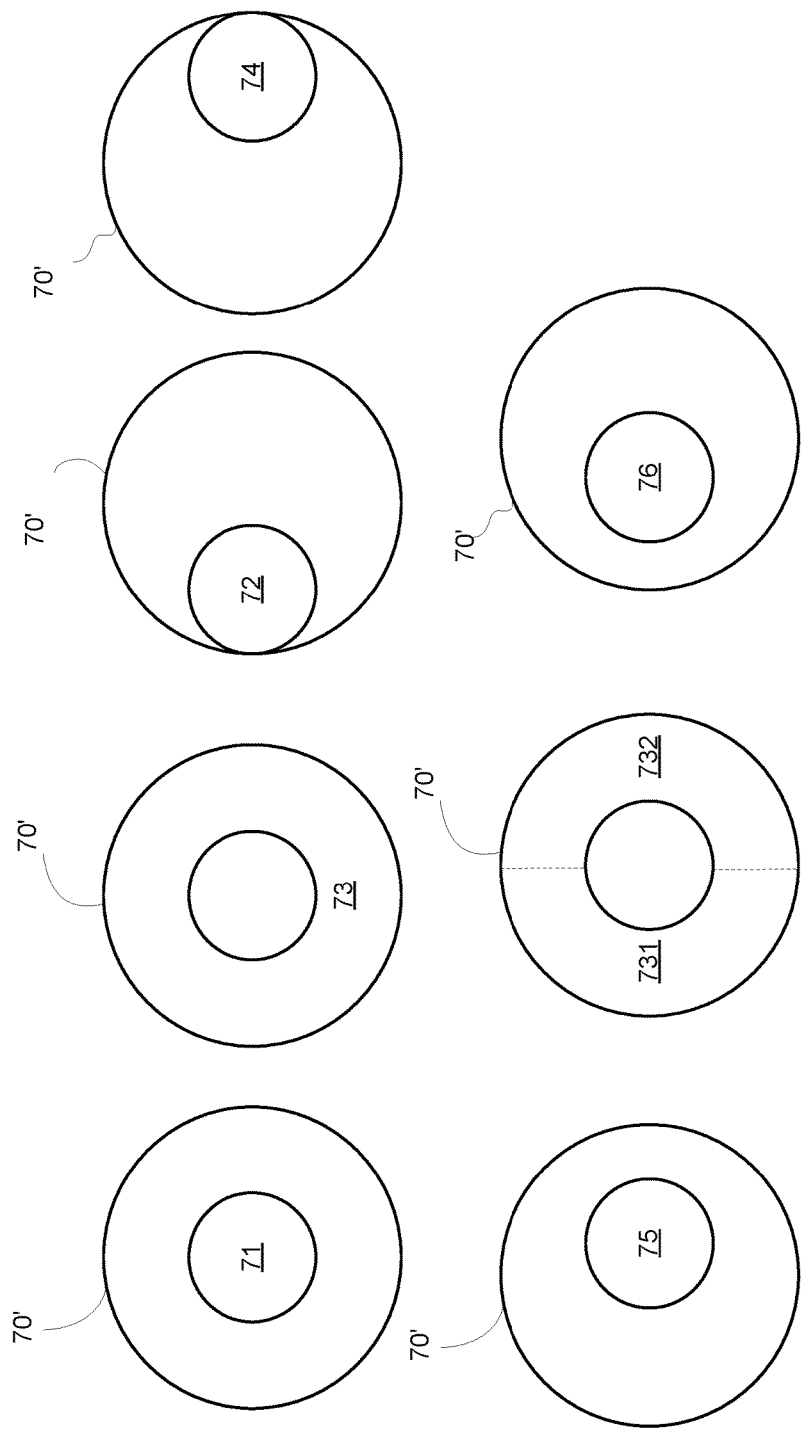
FIG. 20 illustrates various example of an objective lens aperture and various regions of the objective lens.

FIG. 20 illustrates various example of an objective lens aperture 70' and various regions of the objective lens.

The various regions include a first region 71 that is a center region of the objective lens aperture, and various out-of-center regions that include: a second region 72, a third region 73, a fourth region 74, a fifth region 75, a sixth region 76, a seventh region 731, and an eighth region 732.

The objective lens may have regions of shapes and/or size and/or location that differ from those illustrated in FIG. 20. The portions may be located anywhere within the objective lens aperture, may be elliptical, or have any other shape, and the like.

Referring to FIGS. 1-2—the first region 71 is illuminated when the system operates in the first mode, the reflected beam is collected through the first region 71 and the one or more scattered beams are collected by third region 73 or by seventh region 731 and eighth region 731.

Referring to FIGS. 3-4—the second region 72 is illuminated when the system operates in the first mode, the reflected beam is collected through the fourth region 74 and the scattered beam may be collected by first region 71.

Any of these regions may be used for illuminating the object, collecting a reflected beam or collecting a scattered beam.

For example, fifth region 75 may be used, for example, to collect reflected radiation when the sample is not normal to the optical axis of the objective lens.

Figure 21:
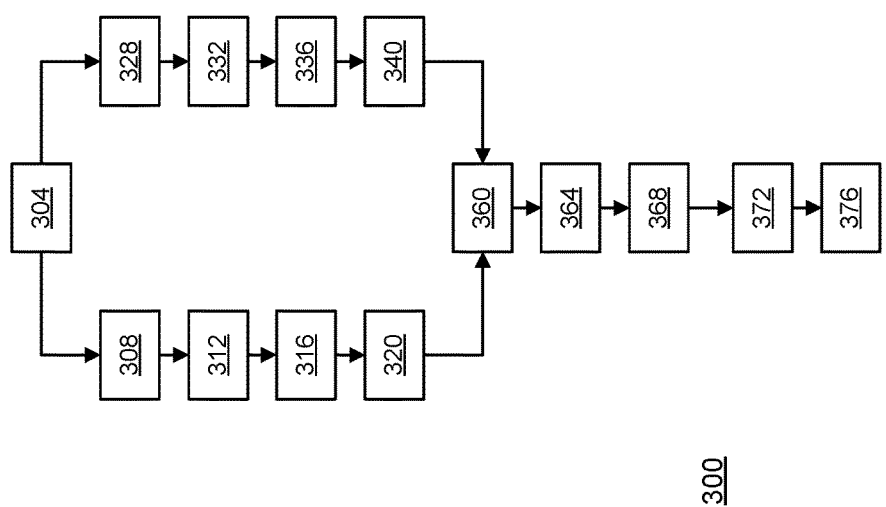
FIG. 21 illustrates a method.

FIG. 21 illustrates an example of method 300.

Method 300 may include steps 304, 308, 312, 316, 320, 328, 332, 336, 340, 360, 364 and 368.

Step 304 may include selecting a mode out of multiple modes. The selection can be made by a human, can be made without human intervention, can be made according to a recipe, and the like. The multiple modes may include a first mode and a second mode. There may be more modes than the first mode and the second mode.

When step 304 included selecting to work in the first mode, step 304 may be followed by step 308 of setting a system to operate in the first mode.

When step 304 included selecting to work in the second mode, step 304 may be followed by step 328 of setting a system to operate in the second mode.

In step 308 and step 328—the setting may include selecting optical elements that will participate in the illumination of the sample and in the collection of radiation from the sample, selecting a required polarization, selecting a position of one or more optical components, selecting a mask, and the like.

Step 308 may be followed by step 312 of providing an input beam, by a radiation source of the system.

Step 312 may be followed by step 316 of directing by optics of the system the input beam through a first opening, without substantially blocking any part of the input beam, towards a first region of the objective lens.

Step 316 may be followed by step 320 of focusing, by an objective lens of the system the input beam directed towards the first region of the objective lens onto the sample at a first angle.

Step 320 may be followed by step 360.

Referring back to step 328—step 328 may be followed by step 332 of providing an input beam, by a radiation source of the system.

Step 332 may be followed by step 336 of directing by the optics the input beam through a second opening, without substantially blocking any part of the input beam, towards a second region of the objective lens. The first region of the objective lens differs from the second region of the objective lens.

Step 336 may be followed by step 340 of focusing, by the objective lens the input beam directed towards the first region of the objective lens onto the sample at a second angle. The first angle differs from the second angle. The difference between the first angle and the second angle may exceed 5, 10, 15, 20, 30 and even more degrees.

Step 340 may be followed by step 360.

Step 360 may include collecting, by the objective lens, a reflected beam that is reflected from the object. Step 360 may also include collecting, by the objective lens, one or more scattered beams that are scattered from the object.

Step 360 may be followed by step 364 of directing the reflected beam and the one or more scattered beams towards the optics.

Step 364 may be followed by step 368 of (a) directing, by the optics, the reflected beam towards a bright field detection module; and (b) directing, by the optics, the one or more scattered beam towards a dark field detection module.

Step 368 may be followed by step 372 of (a) generating detecting signals by the bright field detection module; and (b) generating, detection signals by the dark field detection module.

Step 372 may be followed by step 376 of processing the detection signals generated by the bright field detection module and/or processing the detection signals generated by the dark field detection to obtain information about the sample.

The processing of step 376 may include processing additional information such as reference information, processing computer aided design information, processing detection signals received from an evaluation of another sample, and the like. The processing may include applying any inspection process, any metrology process, any review process, and the like.

Step 376 may be executed by the system or by another computer that does not belong to the system.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A system for multiple mode inspection of a sample, comprising:
   a radiation source that is configured to provide an input beam;
   an objective lens;
   a bright field detection module;
   a dark field detection module; and
   optics;
   wherein the optics, when the system operates at a first mode, is configured to direct the input beam through a first opening, without substantially blocking any part of the input beam, towards a first region of the objective lens;
   wherein the optics, when the system operates at a second mode, is configured to direct the input beam through a second opening, without substantially blocking any part of the input beam, towards a second region of the objective lens; wherein the first region of the objective lens differs from the second region of the objective lens;
   wherein the objective lens is configured to:
   (a) focus the input beam directed towards the first region of the objective lens onto the sample at a first angle;
   (b) focus the input beam directed towards the second region of the objective lens onto the sample at a second angle; wherein the first angle differs from the second angle;
   (c) collect a reflected beam that is reflected from the sample;
   (d) collect one or more scattered beams scattered from the sample;
   (e) direct the reflected beam and the one or more scattered beams towards the optics; and
   wherein the optics are configured to direct the reflected beam towards the bright field detection module, and to direct the one or more scattered beams towards the dark field detection module.

2. The system according to claim 1, wherein the first angle is normal to the sample and the second angle is an oblique angle.

3. The system according to claim 1, wherein when the system operates in the first mode, the objective lens is configured to collect the reflected beam at the first region of the objective lens, and to collect the one or more scattered beams at one or more regions of the objective lens that differ from the first region of the objective lens.

4. The system according to claim 1, wherein when the system operates in the second mode, the objective lens is configured to collect a scattered beam of the one or more scattered beams at the first region of the objective lens, and to collect the reflected beam at a region of the objective lens that differs from the first region of the objective lens.

5. The system according to claim 1 further comprising a telescope, wherein the objective lens is positioned between the sample and the telescope.

6. The system according to claim 5, wherein the telescope comprises multiple lenses; wherein at least two lenses of the multiple lenses are aspheric lenses.

7. The system according to claim 1 further comprising a mechanical manipulator that is configured to change a location of at least one optical component of the optics between the first mode and the second mode.

8. The system according to claim 7, wherein the first opening is formed in a first mask; wherein the second opening is formed in a second mask; and wherein the mechanical manipulator is configured to change positions of the first mask and of the second mask between the first mode and the second mode.

9. The system according to claim 1 wherein the optics comprise at least two movable reflecting mirrors that are movable between the first mode and the second mode.

10. The system according to claim 1 wherein the optics comprise a pair of prisms and a blocking element that is positioned between the pair of prisms.

11. The system according to claim 1 wherein the optics comprise a polarization control unit for controlling a polarization of the input beam.

12. The system according to claim 1 further comprising a polarizer that precedes the dark field detection module; wherein the polarizer comprises a first segment and a second segment; wherein the first segment comprises a first grid of parallel metallic segments; wherein the second segment comprises a second grid of parallel metallic segments; and wherein the first grid is oriented to the second grid.

13. The system according to claim 1 wherein the optics comprise a path compensation unit for compensating for an optical path difference between the first mode and the second mode.

14. A system for multiple mode inspection of a sample, comprising:
a radiation source that is configured to provide an input beam;
an objective lens;
a bright field detection module;
a dark field detection module; and
optics that are constructed and configured, when at a first mode, to direct the input beam towards a certain region of the objective lens;
wherein the objective lens is configured to (a) focus the input beam directed towards the certain region of the objective lens onto the sample at a first angle; (b) collect a reflected beam that is reflected from the object; (c) collect one or more scattered beams scattered from the sample, and (d) direct the reflected beam and the one or more scattered beams towards the optics;

wherein the optics are configured, when at the first mode, to direct the reflected beam towards the bright-field detection module and to direct the one or more scattered beams towards the dark field detection module;
wherein the optics are constructed and configured, when at a second mode, to direct the input beam towards another region of the objective lens; the other region of the objective lens differs from the certain region of the objective lens;
wherein the objective lens is configured to (a) focus the input beam directed towards the other region of the objective lens onto the sample at a second angle; (b) collect the reflected beam that is reflected from the sample; (c) collect the one or more scattered beams scattered from the sample, and (d) direct the reflected beam and the one or more scattered beams towards the optics;
wherein the optics are configured, when at the second mode, to direct the reflected beam towards the bright-field detection module and to direct the one or more scattered beams towards the dark field detection module.

15. A method for multiple mode inspection of a sample by a system, the method comprising:
providing an input beam, by a radiation source of the system;
directing by optics of the system, when the system operates at a first mode, the input beam through a first opening, without substantially blocking any part of the input beam, towards a first region of an objective lens;
focusing, by the objective lens of the system, when the system operates at the first mode, the input beam that is directed towards the first region of the objective lens onto the sample at a first angle;
directing by the optics of the system, when the system operates at a second mode, the input beam through a second opening, without substantially blocking any part of the input beam, towards a second region of the objective lens; wherein the first region of the objective lens differs from the second region of the objective lens;
focusing, by the objective lens of the system, when the system operates at the second mode, the input beam that is directed towards the second region of the objective lens onto the sample at a second angle; wherein the first angle differs from the second angle;
collecting, by the objective lens of the system, when the system operates in the first mode and when the system operates in the second mode, a reflected beam that is reflected from the sample;
collecting, by the objective lens, when the system operates in the first mode and when the system operates in the second mode, one or more scattered beams that are scattered from the sample;
directing the reflected beam and the one or more scattered beams towards the optics;
directing, by the optics, the reflected beam towards a bright field detection module; and
directing, by the optics, the one or more scattered beams towards a dark field detection module.

* * * * *